(12) United States Patent
Tinianov et al.

(10) Patent No.: US 7,055,370 B2
(45) Date of Patent: *Jun. 6, 2006

(54) DEVICE FOR CONDUCTING THE ON-SITE MEASUREMENT OF THE DENSITY OR THERMAL RESISTANCE OF A MATERIAL

(75) Inventors: Brandon Dillan Tinianov, Littleton, CO (US); Francis J. Babineau, Jr., Parker, CO (US); Thomas John Fellinger, Littleton, CO (US); Angela Robin Bratsch, Monument, CO (US)

(73) Assignee: Johns Manville, Denver, CO (US)

(*) Notice: Subject to any disclaimer, the term of this patent is extended or adjusted under 35 U.S.C. 154(b) by 6 days.

This patent is subject to a terminal disclaimer.

(21) Appl. No.: 10/862,203

(22) Filed: Jun. 7, 2004

(65) Prior Publication Data

US 2005/0268696 A1    Dec. 8, 2005

(51) Int. Cl.
*G01N 9/00* (2006.01)
*G01N 15/08* (2006.01)

(52) U.S. Cl. .......................... 73/32 R; 73/38; 73/30.02

(58) Field of Classification Search ............. 73/32 R, 73/38, 30.01, 30.02, 30.04, 64.47
See application file for complete search history.

(56) References Cited

U.S. PATENT DOCUMENTS

| 3,788,125 | A | * | 1/1974 | Kirschstein et al. | ......... 73/32 R |
| 5,005,403 | A | * | 4/1991 | Steudle et al. | ............. 73/61.71 |
| 5,509,295 | A | * | 4/1996 | Bartoli | ...................... 73/30.02 |
| 5,633,453 | A | * | 5/1997 | Johnson | .......................... 73/38 |
| 5,698,772 | A | * | 12/1997 | Deruyter et al. | ............... 73/38 |
| 6,826,920 | B1 | * | 12/2004 | Wacker | ...................... 62/176.6 |

* cited by examiner

*Primary Examiner*—Helen Kwok
(74) *Attorney, Agent, or Firm*—Robert D. Touslee

(57) ABSTRACT

A device suitable for conducting an on-site measurement of the density and/or R-value of a gas-permeable material is provided. The device comprises a chamber comprising a first port and a second port; a diffuser in fluid communication with the second port of the chamber, wherein the diffuser comprises a diffuser port for conveying a gas flow to or from a gas-permeable material, and wherein the area of the diffuser port is greater than the area of the second port; and a pressure sensor arranged to measure the pressure in the chamber.

16 Claims, 2 Drawing Sheets

DEVICE FOR CONDUCTING THE ON-SITE MEASUREMENT OF THE DENSITY OR THERMAL RESISTANCE OF A MATERIAL

BACKGROUND

It can be desirable to determine the characteristics such as the density and/or thermal resistance (R-value) of gas-permeable materials including, for example, thermal and/or sound insulation materials for use in a residential and/or commercial building. Generally, various known methods exist for measuring the density and/or R-value of a material. Some known methods require the removal of a sample of the material from its installed, preferred location and/or the destruction of such sample in order to determine the density and/or R-value thereof. Some known methods do not provide a density and/or R-value measurement that is substantially representative of a large portion of the material or the entire material, and only provide an accurate measurement of a relatively small portion of the material.

A thermal and/or sound insulation product can be formed by blowing insulation material such as fiberglass and an adhesive onto a surface, and curing the applied materials. This method can be used in the formation of, for example, insulation product between wall studs and/or ceiling/floor joists. Methods and systems for forming such an insulation product are discussed in, for example, U.S. Pat. Nos. 4,712,347, 5,287,674 and 5,641,368. The density and/or R-value of such "blown-in" insulation products can depend on the specific manner in which such product is applied on-site. Accordingly, it can be desirable to determine whether such blown-in products meet certain density and/or R-value specifications.

It also can be desirable to measure the density and/or R-value of a gas-permeable material by non-destructive means, and/or without the need for removing such material from its preferred, installed location.

A known method for measuring the density and/or R-value of a gas-permeable material involves using a device which measures the airflow resistance through the gas-permeable material. From an experimentally-derived correlation between airflow resistance, density and R-value, the density and/or R-value can be calculated.

SUMMARY

According to one aspect, a device suitable for conducting an on-site measurement of the density and/or R-value of a gas-permeable material is provided. The device comprises:

a chamber comprising a first port and a second port;

a diffuser in fluid communication with the second port of the chamber, wherein the diffuser comprises a diffuser port for conveying a gas flow to or from a gas-permeable material, and wherein the area of the diffuser port is greater than the area of the second port; and a pressure sensor arranged to measure the pressure in the chamber.

According to other aspects, methods for conducting an on-site measurement of the density and/or R-value of a gas-permeable material using the device described above are provided.

DETAILED DESCRIPTION

Figure 1:
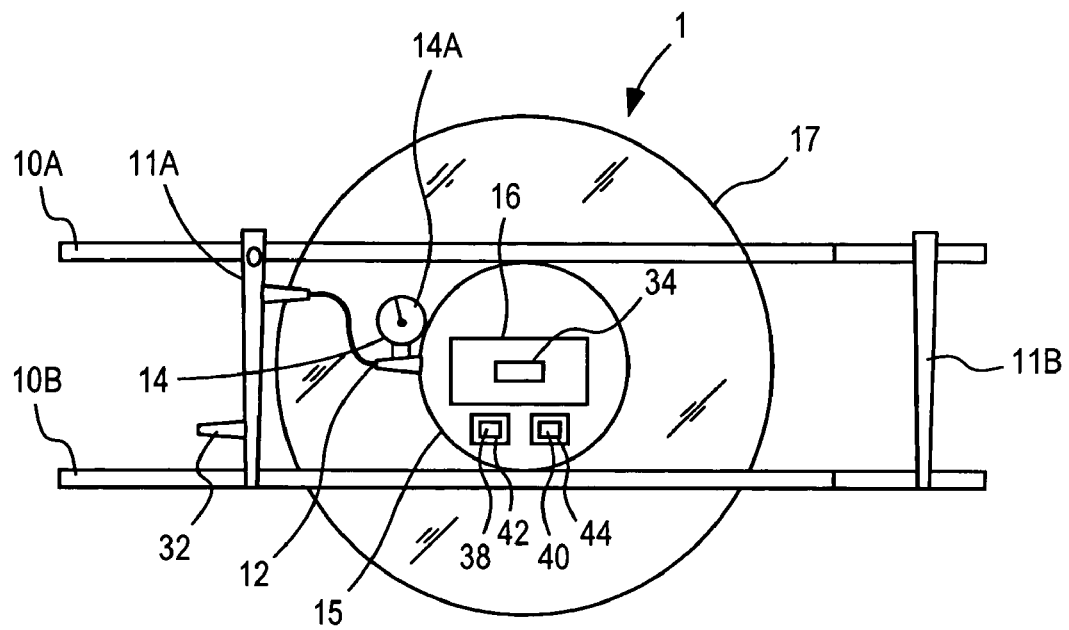
FIG. 1 is a top view of an exemplary device for measuring the density and/or R-value of a gas-permeable material.
Figure 2:
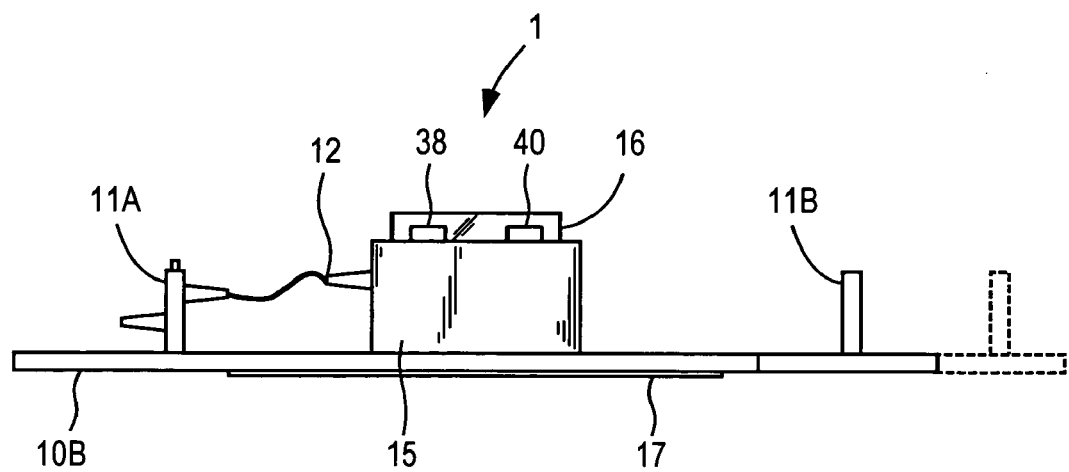
FIG. 2 is a side view of an exemplary device for measuring the density and/or R-value of a gas-permeable material.
Figure 3:
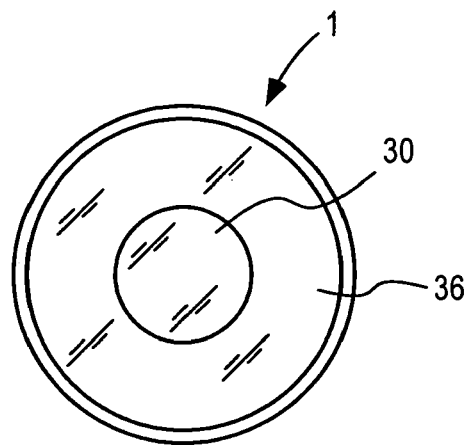
FIG. 3 is a bottom view of an exemplary device for measuring the density and/or R-value of a gas-permeable material.

Devices, systems and methods suitable for measuring the density and/or R-value of a gas-permeable material are provided.

Exemplary embodiments can enable the on-site measurement of the density and/or R-value of the gas-permeable material, for example, at a residential or commercial building at which the material is installed. Preferably, the exemplary embodiments can provide a non-destructive means for measuring the density and/or R-value of the material. Exemplary embodiments can also enable measurement of the density and/or R-value of the material without requiring the removal of such material from a preferred, installed location.

The gas-permeable material can include, for example, a thermal and/or sound insulation material. In an exemplary embodiment, the gas-permeable material excludes materials which do not permit the flow of gas therethrough, for example, a closed-cell foam, impervious reflective insulation and house wrap. Preferably, the gas-permeable material can be formed from at least fiberglass and a binder material. In an exemplary embodiment, the gas-permeable material can include a "blown-in" thermal and/or sound insulation material which is formed by blowing a fiberglass insulation material and an adhesive at a surface to be insulated. For example, the surface to be insulated can include a cavity defined by at least two wall studs and/or ceiling/floor joists. In an exemplary embodiment, the cavity can be defined by adjacent, substantially parallel wall studs.

The gas-permeable material can be a wet-applied material and have a relatively high moisture content prior to being fully cured. An example of a wet-applied material is the blown-in insulation material described above. It can be useful to determine the density and/or R-value of the material prior to, during or after the material is cured. Accordingly, the devices, systems and methods can be used prior to, during or after curing of such wet-applied material. Preferably, the devices, systems and methods can be used after curing.

Referring to FIGS. 1 to 4, a device 1 for measuring the density of a gas-permeable material can include a measuring chamber 15 having a first port 12 and a second port 30. The chamber 15 can have any suitable structure, preferably a structure suitable to accommodate a flow of gas therethrough. Preferably, the chamber 15 can be capable of being sealed such that the first and second ports 12 and 30 provide the only fluid access to the interior of the chamber 15. In an exemplary embodiment, the chamber 15 can have a substantially cylindrical shape. However, the chamber 15 is not limited to having such shape.

The first port 12 can accommodate the flow of gas to and from the chamber 15. That is, the first port can function as both an inlet and an outlet of the chamber 15. The first port 12 can take the form of at least one aperture. For example, the first port 12 can be arranged at a sidewall or at the top of the chamber 15. A valve 14 can be arranged proximal to or at the first port 12 to control the flow of gas through the first port 12. A flow meter 14A can be arranged proximal to the valve 14. The first port 12 can optionally be in fluid communication with a nozzle 32 to facilitate connection thereof to a gas conduit.

In an exemplary embodiment, the first port 12 can function as an inlet and be connected to receive a flow of gas from a gas source (not shown). The gas source can provide a flow of compressed gas to the inlet 12. Any compressed gas having a predetermined pressure can be used such as, for example, compressed air. Preferably, the gas source and/or valve 14 can be controlled to maintain a substantially continuous flow of gas to the first port 12.

In an alternative embodiment, the first port 12 can function as an outlet and be connected to be in fluid communication with a vacuum source (not shown). The vacuum source can induce the flow of gas from the chamber 15 and out of the first port 12. Any suitable vacuum source can be used, for example, Versa-Vac 11 vacuum available from Wm. W. Meyer & Sons Inc., located in Skokie, Ill.

The chamber 15 can include a second port 30 which accommodates a flow of gas to or from the chamber 15. The second port 30 can include a single aperture or a plurality of apertures through which the gas flows, preferably a single aperture. In an exemplary embodiment wherein the chamber 15 is cylindrically shaped, the second port 30 can take the form of an aperture arranged at an end of the cylinder. For example, the area of the aperture can be substantially equal to the area of the end of the cylinder.

A pressure sensor 16 can be provided which is connected to measure the pressure in the measuring chamber 15. For example, the pressure sensor 16 can detect when the pressure in the chamber 15 increases or decreases. The pressure sensor 16 can include a memory device (not shown) to assist in comparing pressure levels over time. In an exemplary embodiment, the pressure sensor 16 can be attached to the chamber 15.

The pressure sensor 16 can take pressure measurements, for example, either continuously or semi-continuously. Conventional pressure sensors which are known in the art can be used in the device 1. For example, a Magnahelic differential pressure gauge available from McMaster-Carr Supply Co. located in Atlanta, Ga., can be used.

The pressure sensor 16 can include an analog or digital display 34 which displays the chamber pressure level. For example, the display 34 can assist a user in monitoring the chamber pressure level. Additionally or alternatively, the pressure sensor 16 can be connected to provide pressure level data to an analyzer.

The device 1 can include a temperature sensor 38 and/or relative humidity sensor 40 that are connected to measure the temperature and relative humidity of the gas in the measuring chamber 15, respectively. Each sensor 38 and 40 can include a memory device (not shown) to assist in comparing levels. In an exemplary embodiment, the sensors 38 and 40 can be attached to the chamber 15. Each sensor 38 and 40 can include a display 42 and 44, and/or the sensors 38 and 40 can be arranged to provide data to an onboard or remote analyzer. The sensors 38 and 40 can take measurements, for example, either continuously or semi-continuously. Conventional temperature and relative humidity sensors which are compatible with the device 1 can be used. For example, a Thermalogic temperature and humidity meter available from McMaster-Carr Supply Co. located in Atlanta, Ga., and a temperature and humidity meter available from Omega Engineering, Inc. located in Quebec, Canada, can be used.

Use of the temperature and/or relative humidity sensors 38 and 40 can improve the accuracy of the density and/or R-value measurement. For example, measuring the relative humidity in the chamber 15 and the temperature of the gas in the chamber 15 can provide an estimation of the moisture content of a wet-applied material (such as a blown-in insulation material) and/or the mass flow rate of the air. Consideration of such parameters can lead to a more accurate density and/or R-value measurement.

A diffuser 17 can be arranged to be in fluid communication with the second port 30 of the chamber 15, preferably in direct fluid communication with the second port 30. The diffuser 17 can have a diffuser port 36 which accommodates the flow of gas to and from the diffuser 17. The diffuser port 36 can comprise a single aperture or a plurality of apertures through which the gas flows. The diffuser 17 can be integrally and permanently connected to the chamber 15, or the diffuser 17 can be integrally connected but separable from the chamber 15 to facilitate maintenance.

In an exemplary embodiment, the area of the diffuser port 36 is greater than the area of the second port 30 of the chamber. For example, the ratio of the area of the diffuser port 36 to the area of the second port 30 can be about 5:1 or greater, preferably about 8:1 or greater, and more preferably about 10:1 or greater. For example, the ratio of the area of the diffuser port 36 to the area of the second port 30 can be about 5:1 to about 20:1, more preferably about 8:1 to about 12:1.

As discussed above, each of the diffuser port 36 and the second port 30 of the chamber 15 can include a single aperture or a plurality of apertures. As used herein, the phrase "area of the diffuser port" refers to the total surface area of the single aperture or plurality of apertures which constitute the diffuser port 36. Likewise, as used herein, the phrase "area of the second port" refers to the total surface area of the single aperture or plurality of apertures which constitute the second port 30.

The diffuser 17 can include a sealing member (not shown) arranged along the periphery of the diffuser 17. The sealing member can, for example, improve the fluid seal between the diffuser 17 and the gas-permeable material when the diffuser 17 is contacted therewith.

In an exemplary embodiment, the diffuser port 36 can accommodate a gas flow through a larger surface area of the gas-permeable material, in comparison with the area of the gas-permeable material that would be exposed by the second port 30. While not wishing to be bound to any particular theory, it is believed that passing the gas flow through a larger area of the gas-permeable material can result in a more accurate measurement of the airflow resistance of the gas-permeable material as a whole. This can in turn lead to a more accurate determination of the density and/or R-value of the material.

In an exemplary embodiment, a flow of gas can be introduced to the chamber 15 via the first port 12 and pass through the diffuser 17 and into the gas-permeable material. The flow rate of the gas exiting the diffuser port 30 can be sufficient to penetrate the surface of the gas-permeable material and provide a pressure differential in the chamber 15. For example, the flow rate of the gas exiting the diffuser port 36 can be about 50 SCF/h to about 400 SCF/h, more preferably about 100 SCF/h to about 200 SCF/h. The pressure sensor 16 can measure the pressure differential in the chamber 15, and the airflow resistance through the gas-permeable material can thus be measured.

In an alternative embodiment, a gas can be drawn at least partially through the gas-permeable material and into the diffuser 17 by force of a vacuum source in fluid communication with the gas-permeable material. The gas flow can pass through the diffuser 17 and into the chamber 15 via the second port 30, and exit the chamber 15 via the first port 12. The pressure sensor 16 can measure the pressure differential in the chamber 15, and the airflow resistance through the gas-permeable material can thus be measured.

In an exemplary embodiment, the device 1 can include at least two rails 10A and 10B which, for example, can be substantially parallel to each other. The rails 10A and 10B can enable the device 1 to be placed in a stable position when measuring an insulation product installed between longitudinally-oriented or latitudinally-oriented studs. Maintaining the device 1 in a stable position during operation can improve the accuracy of pressure measurements taken.

Figure 4:
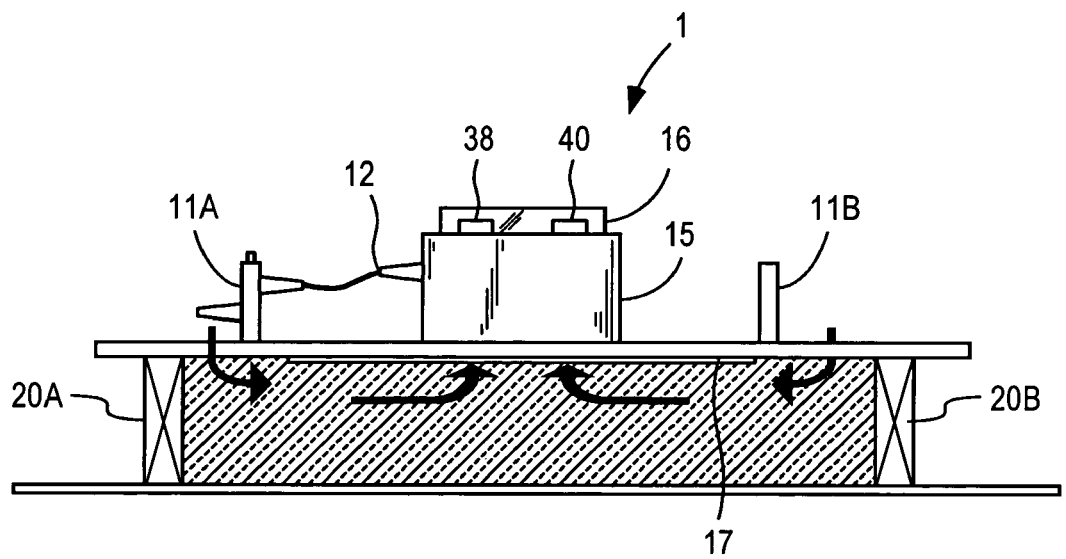
FIG. 4 is a side view of an exemplary device for measuring the density and/or R-value of a gas-permeable material, wherein the device is in contact with the gas-permeable material.

For example, referring to FIGS. 1 and 4, the device 1 can be positioned such that each rail 10A and 10B is in contact with studs 20A and 20B. By positioning the device 1 against the studs 20A and 20B, the device 1 can be maintained at a substantially fixed position during measurement. Handles 11A and 11B can be connected to the rails 10A and 10B to support the rails 10A and 10B and to facilitate holding the device 1 in place.

In an exemplary embodiment, the length of the rails 10A and 10B can be adjusted to accommodate for the specific amount of space between the studs 20A and 20B. For example, 16-inch and 24-inch stud spacing intervals can be used in typical building applications. Each rail 10A and 10B can include a first sliding section and a second sliding section in slideable relation to one another. The sliding sections enable the length of each rail 10A and 10B to be extended or retracted. For example, the handle 11A can be attached to the first section of each rail 10A and 10B, and the handle 11B can be attached to the second section of each rail 10A and 10B. By sliding the handles 11A and 11B closer or further apart, the overall length of the rails 10A and 10B can be reduced or increased, respectively, in order to accommodate for the space between the studs 20A and 20B.

Figure 5:
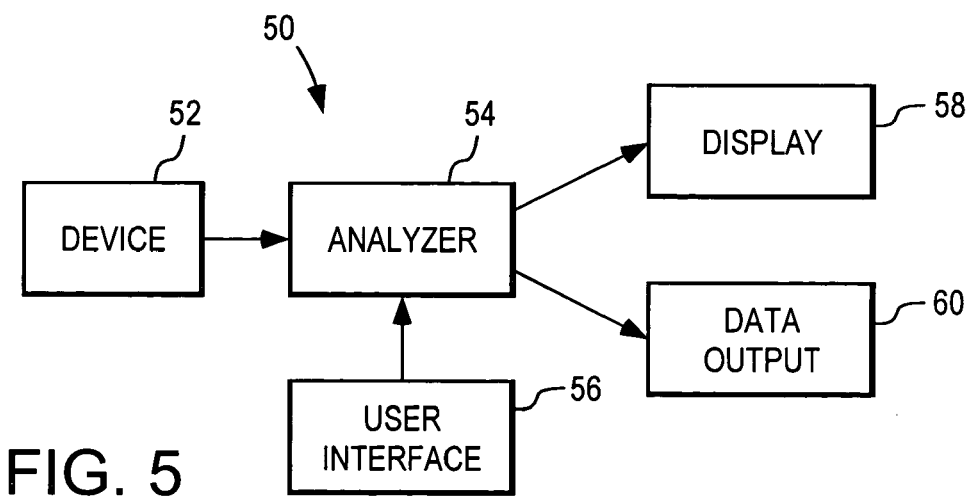
FIG. 5 is a flow diagram of an exemplary system for measuring the density and/or R-value of a gas-permeable material.

In an exemplary embodiment, referring to FIG. 5, a system 50 for measuring the density and/or R-value of a gas-permeable material can be provided. The system 50 can include the device 52 described above and an analyzer 54. For example, the analyzer 54 can include a computer or computer system connected to receive pressure, temperature and/or relative humidity data from the sensors of the device 52. The analyzer can be integrated as a part of the device 52, or can be separate from but arranged to receive data from the device 52, for example, through the use of a hard-wired or wireless connection.

Utilizing the data received from the pressure sensor, temperature sensor and/or relative humidity sensor, the analyzer 54 can determine the density and/or R-value of the material. The analyzer can include a memory device (not shown) for storing data.

The system 50 can include a user interface 56 which enables a user to view data and manipulate the functions of the analyzer 54. The system 50 can further include a display 58 to assist the user and/or a data output means 60. The data output means 60 can include a printer, which can be useful in providing on-site reports of the measurements obtained by the device 52 and/or determinations made by the analyzer 54. For example, by use of a printer, a receipt can be generated on-site verifying the density and/or R-value specification of an insulation material. Such a receipt can be useful to buyers, inspectors, builders and/or regulatory officials.

In an exemplary embodiment, data which correlates the pressure, temperature and/or relative humidity measurements to the density and/or R-value of the material, can be used to determine the density and/or R-value. Generally, such correlation data may be unique to each specific material. Accordingly, the analyzer 54 can contain various sets of data to accommodate for different types of materials (e.g., different makes and manufacturers of materials). Additionally or alternatively, mathematical modeling can be used to estimate the density and/or R-value of the material based on the obtained measurements. In an alternative embodiment, the device can be used apart from the above-described system to obtain measurements which can then be processed using alternative means to determine the density and/or R-value of the material.

In an exemplary embodiment, a method for measuring the density of a gas-permeable material can be provided. For example, the method can utilize the device and/or system described above.

The device can be positioned such that the diffuser thereof is proximal to or in contact with the gas-permeable material, preferably in contact with the gas-permeable material. In one embodiment, the entire outermost portion of the diffuser can be in contact with the gas-permeable material. As used herein, the phrase "proximal to the gas-permeable material" is meant to include any distance from the gas-permeable material which allows the device to obtain substantially accurate pressure, temperature and/or relative humidity measurements. While not wishing to be bound to any particular theory, it is believed that the accuracy of pressure measurements obtained by the device can be diminished if the distance between the device and the gas-permeable material is excessively large.

As discussed above, in an exemplary embodiment, the device and/or system can be used with a gas source such as a compressed gas source.

A first pressure measurement can be conducted while a gas flow is not being introduced into the chamber of the device. For example, the first pressure measurement can be taken before or after the device is positioned proximal to or in contact with the gas-permeable material.

The device can be positioned proximal to or in contact with the gas-permeable material, and a gas flow from the gas source can be introduced to the chamber. A second pressure measurement can be taken while the gas flow is being introduced into the chamber. For example, a gas is able to flow through the gas-permeable material. Preferably, the second measurement can be taken after the chamber has reached steady state with regard to at least one and preferably all of the measured parameters. In the same manner, first and second measurements can be obtained for the temperature and/or relative humidity in the chamber.

In an alternative embodiment, the device and/or system can be used with a vacuum source. A first pressure measurement can be taken while a vacuum source is not being used to draw a gas flow through the device. For example, the first measurement can be taken before or after the device is positioned proximal to or in contact with the gas-permeable material.

The device can be positioned proximal to or in contact with the gas-permeable material, and the vacuum source can be used to draw a gas flow through the device. A second pressure measurement can be taken while the gas flow is flowing through the chamber. For example, a gas is able to flow through the gas-permeable material. Preferably, the second measurement can be taken after the chamber has reached steady state with regard to at least one and preferably all of the measured parameters. In the same manner, first and second measurements can be obtained for the temperature and/or relative humidity in the chamber.

In both of the embodiments discussed above, the presence of the gas-permeable material proximal to or in contact with the diffuser can cause the second measurement(s) to be different from the first measurement(s). Such differential(s) between the first and second measurements can be used to calculate the density and/or R-value of the gas-permeable material.

In light of the above, other features and modifications will become apparent to one skilled in the art.

EXAMPLE

The device shown in FIG. 1 is used to measure the density and R-value of a gas-permeable, fiberglass insulation product. The insulation product is formed by blowing insulation material and an adhesive into a cavity. The device is used anytime after application of the insulation material, preferably after the material is cured. The fiberglass insulation product is present in a cavity defined by two wall studs and a back wall, and the device is used without removal of any of the product from the cavity.

Ambient pressure in the chamber is measured using the device to obtain a first pressure measurement.

Thereafter, the first port of the device is connected to be in fluid communication with a compressed air source. The device is positioned against and in contact with the two wall studs, the diffuser of the device being in contact with the fiberglass insulation product. The compressed air source introduces a flow of compressed air into the chamber of the device, and the air flow passes through the diffuser and penetrates into the insulation product. After the pressure in the chamber substantially reaches steady state, a second pressure measurement is taken.

The first and second pressure measurements are used to determine a pressure differential, and the pressure differential is used in conjunction with correlation data for the specific fiberglass insulation product to determine the density and the R-value of the fiberglass insulation product.

What is claimed is:

1. A device suitable for conducting an on-site measurement of the density and/or R-value of a gas-permeable material, comprising:
    a chamber comprising a first port and a second port, wherein the first port is in fluid communication with the second port via the chamber;
    a diffuser in fluid communication with the second port of the chamber, wherein the diffuser comprises a diffuser port for conveying a gas flow to or from a gas-permeable material, and wherein the area of the diffuser port is greater than the area of the second port; and
    a pressure sensor arranged to measure the pressure in the chamber.

2. The device according to claim 1, wherein the ratio of the area of the diffuser port to the area of the second port is about 5:1 or greater.

3. The device according to claim 2, wherein the ratio of the area of the diffuser port to the area of the second port is about 10:1 or greater.

4. The device according to claim 1, wherein the ratio of the area of the diffuser port to the area of the second port is about 5:1 to about 20:1.

5. The device according to claim 1, wherein the first port of the chamber is connected to receive a flow of air from a compressed air source.

6. The device according to claim 1, wherein the first port of the chamber is in fluid communication with a vacuum source.

7. The device according to claim 1, wherein the chamber and diffuser form an integral part of the device.

8. A device suitable for conducting an on-site measurement of the density and/or R-value of a gas-permeable material, comprising:
    a chamber comprising a first port and a second port;
    a diffuser in fluid communication with the second port of the chamber, wherein the diffuser comprises a diffuser port for conveying a gas flow to or from a gas-permeable material, and wherein the area of the diffuser port is greater than the area of the second port; and
    a pressure sensor arranged to measure the pressure in the chamber,
    further comprising two substantially parallel rails, wherein each rail comprises a first section slideably connected to a second section.

9. The device according to claim 8, further comprising a first handle connected to the first section of each rail, and a second handle connected to the second section of each rail.

10. The device according to claim 9, wherein the first and second handles are substantially perpendicular to each rail.

11. The device according to claim 1, wherein the gas-permeable material comprises a fiberglass insulation material.

12. The device according to claim 1, further comprising a temperature sensor arranged to measure the temperature of a gas present in the chamber.

13. The device according to claim 1, further comprising a relative humidity sensor arranged to measure the relative humidity in the chamber.

14. A device suitable for conducting an on-site measurement of the density and/or R-value of a gas-permeable material, comprising:
    a chamber comprising a first port and a second port;
    a diffuser in fluid communication with the second port of the chamber, wherein the diffuser comprises a diffuser port for conveying a gas flow to or from a gas-permeable material, and wherein the area of the diffuser port is greater than the area of the second port; and
    a pressure sensor arranged to measure the pressure in the chamber,
    wherein the device is positioned adjacent to a cavity defined by at least two horizontally or vertically oriented struts.

15. A method for conducting an on-site measurement of the density and/or R-value of a gas-permeable material using the device of claim 1, comprising:
    measuring the pressure in the chamber while a gas flow is not being introduced into the chamber to obtain a first pressure measurement;
    positioning the diffuser proximal to or in contact with a gas-permeable material;
    introducing a gas flow into the chamber;
    measuring the pressure in the chamber while the gas flow is being introduced into the chamber to obtain a second pressure measurement; and
    determining a pressure differential based on the first and second pressure measurements.

16. A method for conducting an on-site measurement of the density and/or R-value of a gas-permeable material using the device of claim 1, comprising:

measuring the pressure in the chamber while a vacuum source is not drawing a gas flow through the chamber, to obtain a first pressure measurement;

positioning the diffuser proximal to or in contact with a gas-permeable material;

drawing a gas flow through the chamber using a vacuum source;

measuring the pressure in the chamber while the gas flow is being drawn through the chamber to obtain a second pressure measurement; and determining a pressure differential based on the first and second pressure measurements.

* * * * *